United States Patent [19]

Posgay et al.

[11] Patent Number: 5,992,241

[45] Date of Patent: Nov. 30, 1999

[54] METHOD AND DEVICE FOR DETERMINING THE NEUTRAL TEMPERATURE OF WELDED TRACKS

[75] Inventors: Gyorgy Posgay; Peter Molnar, both of Budapest; Ferenc Varga, Debrecen; Tibor Zsakai; Alfonz Szamos, both of Budapest; Janos Beli, Dunakeszi; Jozsef Vegi, Budapest, all of Hungary

[73] Assignee: Magyar Allamvasutak Reszvenytarsasag, Budapest, Hungary

[21] Appl. No.: 08/945,985

[22] PCT Filed: May 9, 1996

[86] PCT No.: PCT/HU96/00027

§ 371 Date: Jan. 26, 1998

§ 102(e) Date: Jan. 26, 1998

[87] PCT Pub. No.: WO96/35947

PCT Pub. Date: Nov. 14, 1996

[30] Foreign Application Priority Data

May 9, 1995 [HU] Hungary ................................ 95 01371

[51] Int. Cl.⁶ ...................................................... G01B 7/24
[52] U.S. Cl. .............................................. 73/779; 324/209
[58] Field of Search .............................. 73/763, 766, 779, 73/862.69; 324/209

[56] References Cited

U.S. PATENT DOCUMENTS

| 5,161,891 | 11/1992 | Austill | 73/146 |
| 5,166,613 | 11/1992 | Perry | 324/209 |
| 5,195,377 | 3/1993 | Garshelis | 73/862.69 |
| 5,280,725 | 1/1994 | Stengel | 324/209 |

*Primary Examiner*—Max Noori
*Attorney, Agent, or Firm*—Young & Thompson

[57] ABSTRACT

A method for determining the longitudinal loading acting on a beam, such as a rail of a railway track subjected to longitudinal loading and, in particular, for determining the neutral temperature of railway tracks. The beam is energized longitudinally in the acoustic frequency range, and the level of magnetic Barkhausen noise at the surface of the energized region is measured. Measurements of the magnetic Barkhausen noise are taken for different longitudinal stress states and used for plotting the calibration curve of the magnetic Barkhausen noise as a function of longitudinal stress, the Barkhausen noise being measured at least at three points on the face of the built-in beam, and the calibration curve is used for determining the longitudinal loading on the cross-section in question using weighted averaging. The neutral temperature of the railway track is then calculated considering the modulus of elasticity, coefficient of thermal expansion and temperature of the rail.

7 Claims, 7 Drawing Sheets

METHOD AND DEVICE FOR DETERMINING THE NEUTRAL TEMPERATURE OF WELDED TRACKS

BACKGROUND OF THE INVENTION

The invention relates to a method and equipment for determining the longitudinal loading acting on a beam, such as on a rail of a railway track subjected to longitudinal loading and for determining more particularly the neutral temperature of railway tracks, by energizing the beam longitudinally in the audio-frequency range and measuring the level of Barkhausen noise at the surface of the energized region. Further subject of the invention is an equipment serving for implementing the proposed method.

In the elements used in the construction of track structures lower or higher residual stresses are present due to processes of manufacturing. Further mechanical stresses are added to these residual stresses by dead weight and installation. From the points of view of loadability and fatigue of structural parts, the overall resultant of all these stresses are to be taken into account. However, to find the balance of forces acting on a structure, the force arising in each individual element has to be determined.

The task of determining the forces acting in the various beams of a lattice truss or in a rail of a continuously welded railway track is not a simple technical problem. Application of destructive test methods is not expedient, because, for instance, in the case of a railway track such a test would require setting of scotch blocks.

In a welded track the sleepers prevent displacement of rails through the track fastening elements. After the rails have been clamped, any temperature change causes a thermal stress in the rails due to restriction of dilatation. The temperature at which the thermal stress in the tested cross-section of a rail is zero is termed neutral temperature. It is important that the neutral temperature be in the vicinity of the average of expectable highest and lowest rail temperatures. Should the discrepancy from that average be large, at low temperatures rail ruptures, at high temperatures rail buckling may occur.

In a given cross-section of a rail, stresses may be present even at neutral temperature, resulting from production technology (e.g. due to uneven quenching rate) or installation activities (bending of rails). Characteristic of these stresses is that their resultant referred to the entire cross-sectional area is zero.

For a given cross-sectional area the neutral temperature can be determined from the resultant of stresses arising in the given cross-section.

Non-destructive methods are based on the measurement of a physical characteristic correlated with the stress state of the section of material investigated. A common feature of all such methods is that the correlation is always associated with the actual stress state, and is dependent on the structure of the material concerned (chemical composition, texture, etc.)

The texture of metal and its residual stress depend on the applied manufacturing technology, while the distribution of residual stress may be subject to considerable changes in the course of service—especially during the early years of operation—in a way depending on the location of rails within the track and on the duty imposed on them.

One of the known non-destructive methods is based on the stress-dependence of the level of magnetic Barkhausen noise (Pashley, R. L.: Barkhausen effect—an indication of stress, Materials Evaluation, Vol. 28, No. 7, pp. 157 to 161, 1970).

Magnetic reversals taking place in ferromagnetic materials generate high-frequency electromagnetic and acoustic response signals termed Magnetic Barkhausen Noise. The level of noise depends on the structure of material and its stress state. The stress test performed by measuring the Barkhausen noise is based on the correlation existing between the level of Barkhausen noise and the stress state of the material. Application of Barkhausen noise to stress-state measurements is described in Patent Specification U.S. Pat. No. 4,634,976 and in an international patent application No. PCT/US89/01539. Common feature of the two proposed methods is that the correlation existing between noise level and stress state of a material is determined on a test piece taken from the original component or on a metal sample having a structure identical with the original by means of performing a so-called calibrating measurement.

For measuring the Barkhausen noise, the magnetic polarity of the material is periodically reversed, generally by applying an energizing field of sinusoidal or triangular shape alternating at a frequency between 10 to 100 Hz, causing emission of a high-frequency electromagnetic response signal. The response signal is detected generally by a measuring coil, typically in a frequency band ranging from a few 100 Hz up to a few 100 kHz.

For the measurement of magnetic Barkhausen noise devices of several types are available (e.g. STRESSCAN type device offered by the US firm AST. or STRESSTEST type of the Hungarian firm METALELEKTRO).

A further non-destructive method is disclosed in U.S. Pat. No. 4,405,160 according to which a specimen is magnetically excited at different points and the acoustic Barkhausen noise induced thereby is detected. By applying numerous different both positive and negative (compressive and tensile) loadings a calibration diagram can be drawn and using this calibration diagram the stress can be defined at each individual point.

This known method can be used for evaluation of the loading of a beam under laboratory conditions only. The reason for this lies in that the local maximum of the dependence of the acoustic Barkhausen noise versus stress is at the zero value of the stress, i.e. two, a positive and a negative, stress values belong to the same value of the noise. In order to be able to differentiate the (positive or negative) sense of the stress each measuring point has to be exposed both to positive and negative as well as zero stress. So as to expose each measuring point to zero stress an additional loading has to be applied onto the beam which causes a stress greater than the sum of residual stress caused by manufacture and the stress caused by ordinary loading.

Applying an additional load on a built-in beam is not allowable as being dangerous on one hand, nor can it be practically carried out on the other.

Detecting acoustic Barkhausen noise is influenced by a number of conditions, e.g. the geometric of the specimen, the resonances and reflections inside the specimen and depending on the geometry, surface roughness, contamination and corrosion of the specimen, and acoustic coupling of the sensor for detecting the Barkhausen noise to the specimen. These influences can in practice not be taken into consideration if a built-in beam is tested.

Because of the above conditions, this known method cannot be used to determine the loading of a built-in beam.

SUMMARY OF THE INVENTION

The aim of the present invention is to facilitate practical application of the known measuring principle by proposing a method by which the longitudinal loading of built-in beams or the neutral temperature of railway tracks can equally be determined.

The method complying with the invention is, on the one hand, a method applicable to determining longitudinal loading of beams and, on this basis, in particular, to find the neutral temperature of railway tracks. In the course of performing the method, the support beam is longitudinally energized in the audio-frequency range, and the level of magnetic Barkhausen noise generated at the surface of the energized region is measured. Based on the measurement of magnetic Barkhausen noise performed at various longitudinal stress states, the calibration curve of the longitudinal stress dependence of magnetic Barkhausen noise is plotted. By a suitable method, this calibration curve may equally be plotted for a built-in beam or a rail, loaded longitudinally to an unknown magnitude. In the following at least at three points of the cross-sectional area of the built-in beam the value of Barkhausen noise is measured, and the longitudinal loading acting on the given area is determined on the basis of the calibration curve, applying weighted averaging, if necessary. If the measurement is performed at three points only, these should be selected to lie at the sites of maximum tensile stress and maximum compressive stress and in the transitory area between the regions of the two stresses of opposite sense.

The calibration curve can be plotted in several ways. For this purpose application of at least two different longitudinal loadings is required, but knowledge of the difference between the two different loadings is also sufficient. This can be obtained by applying an additional longitudinal loading of known magnitude. The magnitude of this additional loading is identical with the applied force that can be determined e.g. by means of a strain gauge attached to the beam and by an evaluating unit pertaining to it. Of course, for this evaluation the cross-sectional area of the beam and its modulus of elasticity must be known.

To plot the calibration curve, the magnitude and variation of Barkhausen noise is measured in several points within the same cross-sectional area of the installed beam at least at two different loadings. The two different loadings modify the resultant local longitudinal stresses in the measured points of the beam, these stresses in each point being the algebraic sum of the stress caused by the applied load and of the residual stress of manufacturing. The probability of equality of the resultant longitudinal loading at two different points is low, so the results will differ from each other for the two stress states, and also for each point different levels of Barkhausen noise and different changes in the value of Barkhausen noise will probably be obtained. From the values obtained, the curve showing the level of Barkhausen noise in the function of the magnitude of its variation can be plotted, this function being a two-valued function. The two-valued function shows maximum variation where the stress is zero. Hence, the level of Barkhausen noise pertaining approximately to the state of zero stress is the one that is measured at this point. This value defines one point of the Barkhausen noise vs. stress curve, and in the knowledge of this point, by integration of the inverse function of the two-valued function, the Barkhausen noise vs. stress curve can be set up. From that curve the stress state of the various points of the measured cross-sectional area can be determined.

For producing the Barkhausen noise, the beam is preferably energized in the direction perpendicular to the measured cross-sectional area through two regions spaced some distance apart, and the magnetic Barkhausen noise emitted from the surface is measured at the tested cross-section located between said two regions. The beam is energized by the flux produced by a magnetic yoke attached to the surface, and in order to improve the accuracy of measurement, the magnitude of said flux stepping out at the ends of the yoke fitted to the measured surface is controlled. Thereby the magnitude of excitation can be stabilized.

The magnetic Barkhausen noise is measured at the surface with a sensor containing a ferromagnetic material and matched to the given cross-sectional area. Imperfect matching (due to unevenness of surface, scale, rust, contamination or paint coating) reduces the magnitude of the detected Barkhausen noise. In order to eliminate inaccuracies resulting from such deficiencies, the spacing between the ferromagnetic material and the investigated surface—the so-called air gap—is measured, and the magnitude of the detected magnetic Barkhausen noise is corrected according to the measured depth of the air gap. Measurement of the air gap can be accomplished e.g. by magnetically energizing the ferromagnetic material of the sensor and by magnetic coupling of said material to the measured beam, and observing the growth of stray flux at the surface of the ferromagnetic material in the course of energizing.

Further, to achieve the set aim, a device has been developed for determining the longitudinal loading of longitudinally loaded beams, in particular of railway tracks, for determining neutral temperature of rails of railway tracks. This device contains an audio-frequency energizing unit, a magnetic sensor that can be magnetically coupled to the beam to be measured, a measuring unit coupled to the magnetic sensor sensitive to higher frequencies than the frequency of said energizing unit, as well as a unit for computing the measuring results from the measured values. According to the invention, an air gap measuring unit is associated with the magnetic sensor for sensing the size of spacing between the sensor and the surface of the beam to be measured, said measuring unit being connected to the input of said computer unit correcting the measured level of Barkhausen noise in a way depending on the depth of the air gap.

The energizing unit expediently incorporates an energizing coil connected to the audio frequency generator and arranged on a magnet yoke, and a coil system consisting of coils also accommodated on the same yoke, adjacent to the energizing coil, and arranged at the surfaces of the yoke to be brought into contact with the surface of the beam to be measured. This coil system is suitable for sensing the flux generated by the energizing coil and passing from the yoke to said beam, and, inserted into a suitable control circuit, it stabilizes the energizing flux in the beam.

A preferred embodiment of the magnetic sensor comprises a sensing coil system arranged on a ferromagnetic yoke having at least three limbs and containing coils accommodated in a measuring head. The voltages induced by the local magnetic Barkhausen noise in the two coils will, with high probability, differ from each other and, though the difference between them will be somewhat lower, still the difference will reflect well the noise level. In the beam, especially in rails, however, also electromagnetic disturbance signals may appear e.g. caused by through-flowing currents, yet the voltages induced by such signals will be—with high probability,—of similar magnitude, wave shape and phase in the two coils. Connecting the two windings in opposition, said disturbance voltages will subtract from each other, and their magnitude will considerably decrease. With such coil, arrangement the external disturbance signal can be suppressed considerably.

The device may be completed with templates matched to the different shapes of beams, with positioning elements provided on them defining location of individual measuring points along their cross-sectional area. On the measuring head the configuration can be arranged to follow the pattern of the positioning elements. One simple arrangement, if the outline of the measuring head is asymmetrical, is to provide openings on the template matched to the outline. Thus, the measuring template attachable to the beam is matched to the measuring head as well, and on the measuring template positioning elements, expediently, openings mentioned above are provided, permitting the measuring head to be fitted to the beam in its predetermined position.

The air gap gauge comprises an energizing unit linked up with the energizing coil expediently arranged on the magnetic sensor, together with detectors for sensing the stray flux generated by the energizing coil. As detectors e.g. coils or Hall probes may be used.

BRIEF DESCRIPTION OF THE DRAWINGS

In the followings, the invention will be described in some detail with reference to an embodiment presented as an example in the attached drawing, where.

DESCRIPTION OF THE PREFERRED EMBODIMENTS

Figure 1:
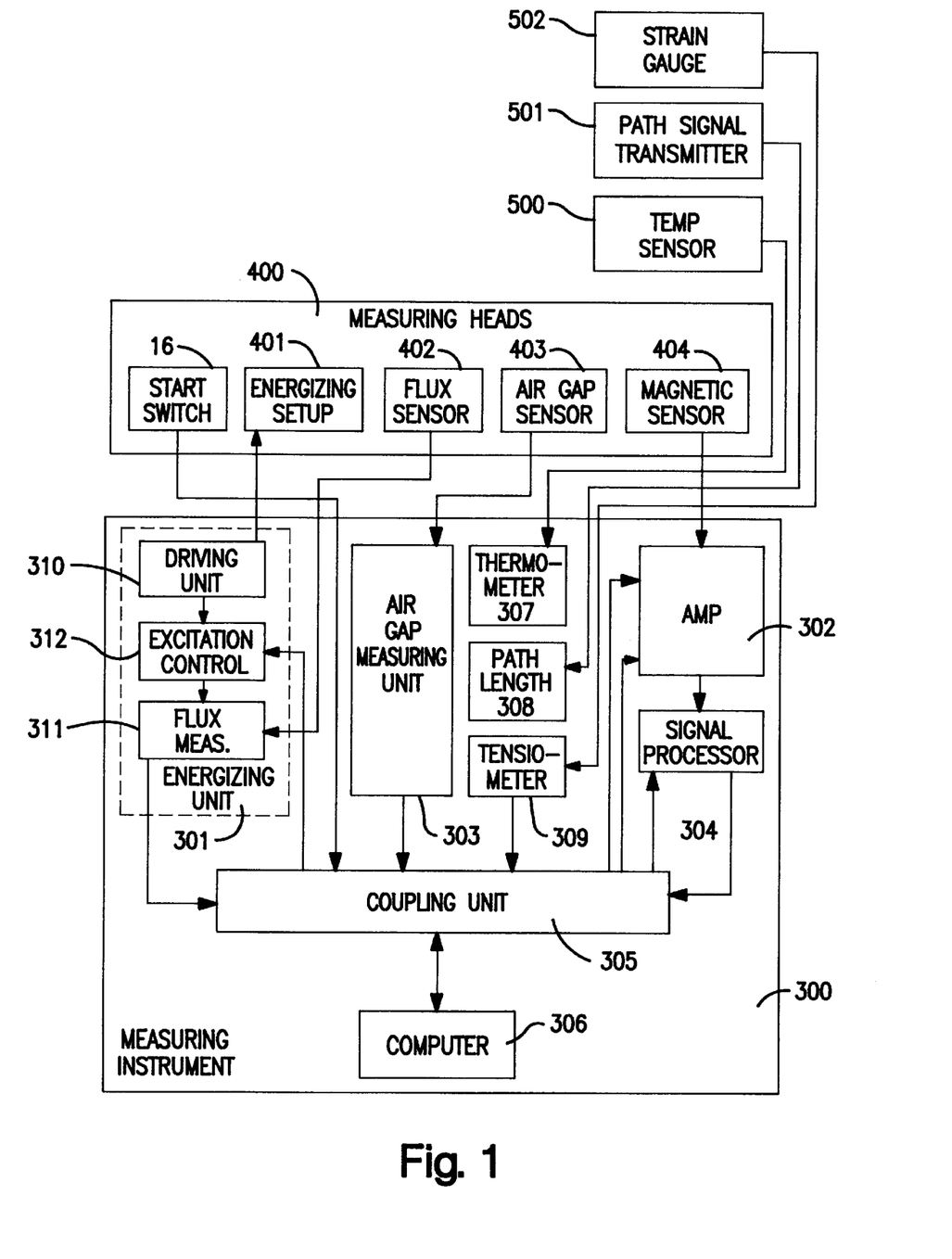
FIG. 1 is the block diagram of the equipment complying with the invention.

The block diagram of the equipment complying with the invention is shown in FIG. 1. The apparatus consists of measuring instrument 300 with one or more measuring heads 400 connected to it by means of wiring and, depending on application, comprises a temperature sensor 500, a path signal transmitter 501 and a strain gauge 502. A measuring template not shown may be attached to the measuring head.

The temperature sensor 500 comprises an electric component, e.g. a thermistor, providing with acceptably low sluggishness an electric signal proportional to the temperature of the structure within the service temperature range of the tested structure.

The path signal transmitter 501 serves for measuring the longitudinal position and distance of measuring points over the tested surface, e.g. by means a pulse transmitter driven e.g. by a friction gear.

Tensiometer 502 issues a signal proportional to the stress varying under the effect of the force acting on the tested beam or rail. The tensiometer may take the form of a strain gauge attached to the beam to be tested.

Measuring instrument 300 contains an energizing unit 301, a frequency-selective amplifier 302, an air gap measuring unit 303, a thermometer unit 307, a path length measuring unit 308 and a tensiometer unit 309. Output of amplifier 302 is linked up with a computer 306 through a signal processing unit 304, whereas the outputs of units 301, 303, 307, 308 and 309 are connected to said computer either directly or through a coupling unit 305 suitable for bi-directional data transmission, if required, incorporating also A/D or D/A converters. Combined with the coupling unit 305 jointly used by other units and with the computer 306, the amplifier 302 and the signal processing unit 304 constitute a frequency-selective measuring unit.

The energizing unit 301 contains a driving stage connected to the excitation control unit 312 linked up with the flux measuring unit 311.

The measuring head 400 consists of an the energizing setup 401, a flux sensor 402, an air-gap sensor 403 and a magnetic sensor 404, as well as a start switch 16.

Figure 2:
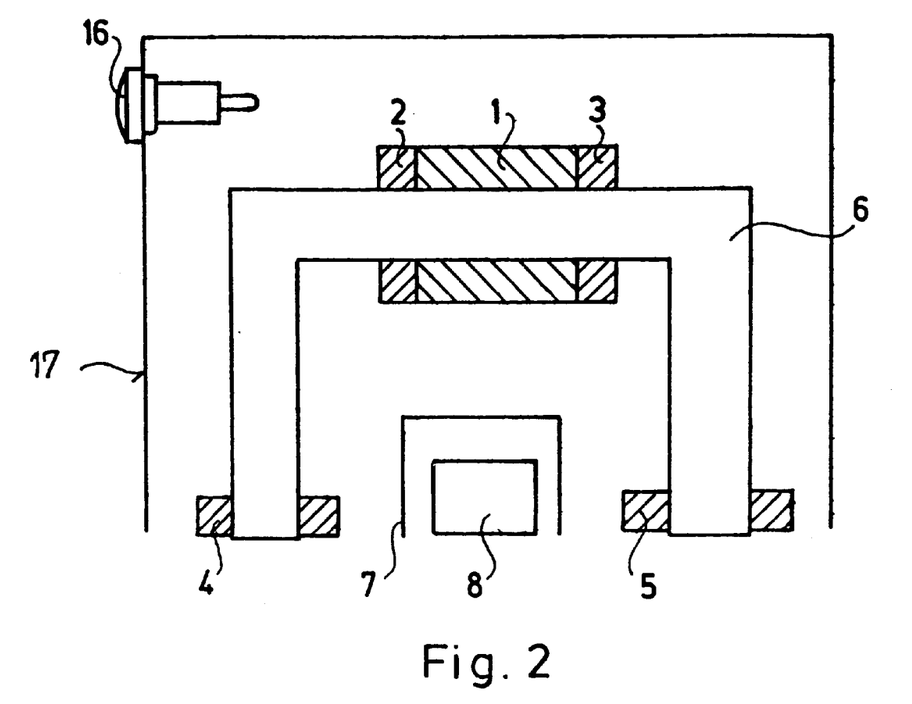
FIG. 2 is the sectional arrangement of the measuring head complying with the invention.

The detailed constructional setup of a preferred embodiment of the measuring head 400 is shown in FIG. 2. The energizing setup 401 of the measuring head 400 consist of an energizing coil 1 arranged on the U-shaped magnet yoke 6, and, further, contains sensor coils 2 and 3 arranged directly beside said energizing coil 1, and sensing coils 4 and 5 placed over the ends of the limbs of magnet yoke 6. The ends of the limbs of magnet yoke 6 can be attached to the measured beam, and its material is preferably iron, e.g. transformer sheet, of high permeability and high saturation value. The flux induced by energizing coil 1 is detected by sensing coils 2 and 3. In the sensing coils 4 and 5 located at the ends of magnet yoke 6 a signal proportional to the flux leaving magnet yoke 6 at the ends of its limbs is generated. In that region the flux enters practically the material of the investigated beam, so the signal generated in sensing coils 4 and 5 is proportional to the magnitude of the magnetic field acting on the material under test.

The sum of signals—henceforth termed flux signals—generated in sensing coils 4 and 5 is led into the flux measuring unit 301, by which—through the action of excitation control unit 312—the output signal of the driving unit 310 as to make the magnitude of excitation of energizing coil 1, sensed by sensing coils 4 and 5, assume a value corresponding to the desired level.

Correlation between flux and the magnitude of reverse magnetization is improved, if the coil or electric component is made sensitive to the flux stepping out in the direction of the region of material seen by the probe serving for measuring the magnetic Barkhausen noise.

The difference between sum of signals generated in sensing coils 2 and 3 and sum of signals generated in sensing coils 4 and 5—hereinafter called air-gap signal—is proportional to the flux closing in the air between the limbs of magnet yoke 6. The flux closing between the limbs of magnet yoke 6 increases, if the average of distances between the limbs of magnet yoke 6 and the investigated material grows, i.e. the air gap increases, so the air gap signal will be proportional to the depth of the air gap.

The air gap signal is led to the air gap measuring unit 303, where—after amplification and required frequency filtering,—a suitable characteristic of said signal, e.g. r.m.s. or absolute average, is formed. The characteristic thus obtained is fed, through coupling unit 305 and after A/D conversion, into computer 306.

Instead of the sensing coils 2 to 6, Hall probes inserted into notches provided in the material of magnet yoke 6. or other electric means suitable for measuring magnetic field strengths may be used.

The electromagnetic waves produced by the effect of magnetic reversal of excitation are detected by probe 8 constituting a magnetic sensor 404. This may be a Hall probe, or a coil where the use of a flux-conducting iron core may be expedient.

Figure 3:
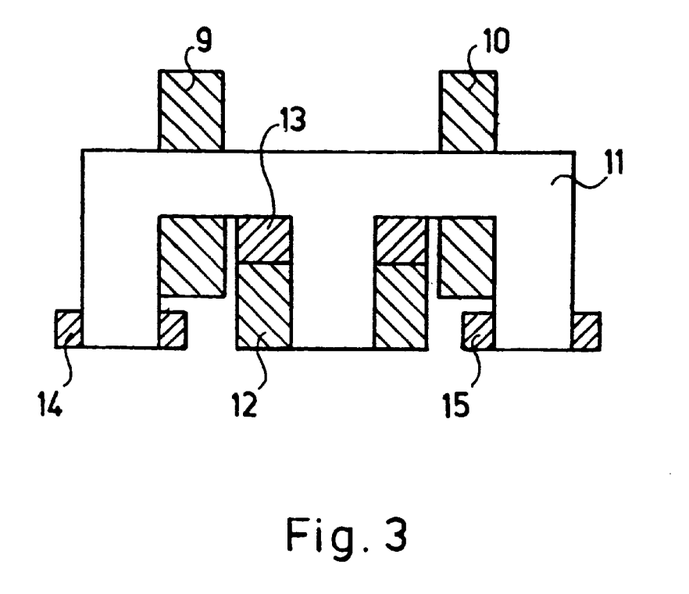
FIG. 3 is a variant of the magnetic sensor of the measuring head of FIG. 2. combined with an air gap gauge, shown in the form of a simplified sectional drawing.

An advantageous embodiment of the magnetic sensor 404 is shown in FIG. 3. Here coils 9–10 accommodated on an E-shape iron core 11 are used. The iron core is a soft-iron, high-frequency magnetic material of low intrinsic Barkhausen noise, e.g. a powdered-iron or nanomagnetic core material.

By connecting the coils 9–10 in opposition, i.e. using them in subtractive connection, they become especially suitable for achieving extinction of cyclic electromagnetic signals to reduce the disturbing effects resulting from excitation of external origin or due to alternating currents flowing in the tested object.

The probability of symmetry or coincidence of inductions closing through coils 9 and 10 and of inductions resulting from magnetic Barkhausen noise of local character is low, therefore no substantial loss of signals caused by the subtractive connection of coils 9 and 10 is to be expected when determining the changes of induction attributable to noise effects, hence when measuring the magnetic Barkhausen noise.

Additional noise reduction results from the use of a screening cup 7 surrounding the probe 8, the material of which is selected expediently according to the characteristic disturbance frequencies. In the case of low-frequency disturbances, the use of some soft magnetic material is recommended, whereas in cases of high frequency disturbances a material of high electric conductivity is to be preferred., The measuring head 400 is enclosed in a casing 17, material of which provides additional screening. On casing 17 a start push-button 16 is provided.

The electric signal generated in probe 8 in led into amplifier 302 tuned to the frequencies matched to the frequency spectrum of the magnetic Barkhausen noise. In the unit, by expedient selection of the elements of a series of amplifiers and band filters, the required amplification can be achieved in the frequency range free of the presence of disturbance signals.

In order to obtain the required band width, the knowledge of the effects of currents flowing in the object to be tested and of external electromagnetic fields is necessary. These effects can be determined by adjusting the measuring head into measuring position and by measuring the frequency spectrum of the signal generated in the probe, without applying excitation. In the knowledge of the frequency spectrum thus obtained, in order to achieve satisfactory signal-to-noise ratio, low-pass and high-pass filters and band filters are applied. Owing to the currents flowing in the tracks of the Hungarian State Railways and to avoid the interference effects of broadcasting stations, the measurement of magnetic Barkhausen noise is carried out in the frequency range of 32 to 250 kHz.

After amplifier 302 the signal is fed into the signal processing unit 304, where some selected characteristic, such as peak, r.m.s. or absolute mean value of the signal, is formed.

The characteristic thus obtained is led into the coupling unit 305, where also the task of A/D conversion is performed.

It is known that in a given material, in a given stress state and under identical external conditions, the magnitude of magnetic Barkhausen noise at constant direction of the reversing magnetic field is dependent on the magnitude of the reversing magnetic field (flux). To make the level of reverse magnetization in the tested object independent of the spacing between measuring head and test piece, i.e. of the air gap, the excitation is reduced to the level of the flux signal. This is done by the excitation control unit 312 comparing a selected characteristic (peak, r.m.s. or absolute mean value) of the flux signal obtained from the flux measuring unit with the signal of the excitation level adjusted by the computer 306 and provided by one of the D/A converters of the coupling unit 305.

By stabilizing to the level of the flux signal, in the case of sufficiently high excitation capability, it can be achieved that in practice, independently of the paint coating and improper matching between measuring head and tested piece, the level of reversed magnetization will correspond to the set value.

Figure 4A:
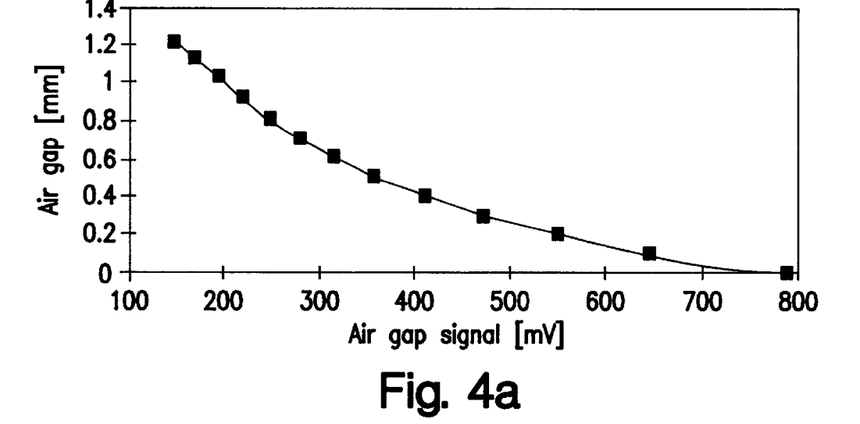
FIGS. 4a to 4c are diagrams serving as basis to perform calibration by means of an air gap gauge.
Figure 4B:
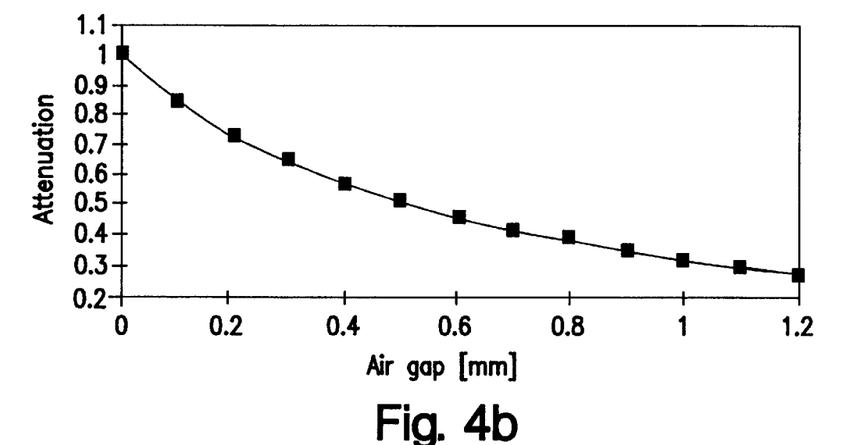
Figure 4C:
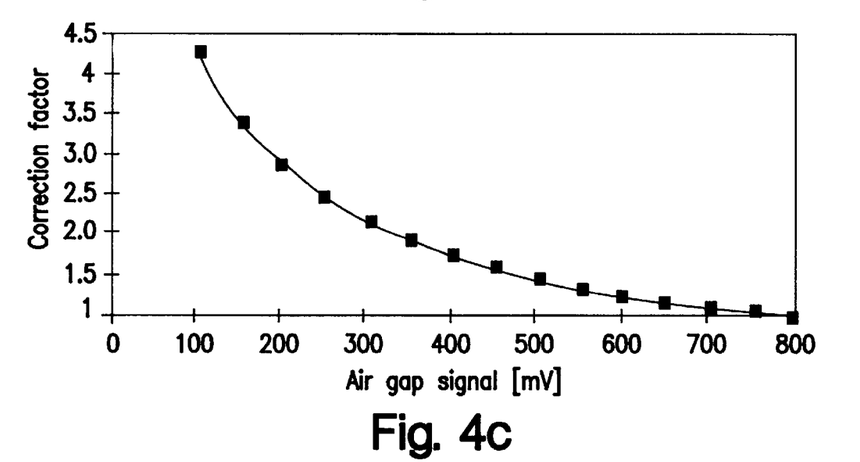

Of course, the level of magnetic Barkhausen noise detected by probe 8 depends on the distance (air gap) between measuring head and tested piece, this effect can be taken into account also when measuring the change taking place in the level of magnetic Barkhausen noise detected by the probe in the function of the air cap. This procedure is termed air-gap calibration. At air-gap values preset at the excitation level desired in the course of air-gap calibration, the characteristics of the air-gap signal and those of the signal generated in probe 8 are measured. Based on the functional relation thus obtained, in the knowledge of the air-gap signal in the course of measurement, the Barkhausen noise level can always be converted to an air-gap value. This conversion will henceforth, be called "air-gap correction" (FIG. 4).

The air-gap signal can be used to warn the personnel performing the measurement, that the spacing between measuring head and tested surface would cause a measuring error that cannot be corrected.

In the case when the tested surface between the energizing limbs of measuring head 6 is not sufficiently smooth, or e.g. the thickness of paint coating varies, the distance of probe 8 from the tested surface fails to be equal to the average the distance of limbs measured from the tested surface. From that it follows that the air-gap correction based on the air-gap signal measured on the limbs of yoke 6 will not be sufficiently accurate. The correlation of the signal of probe 8 with the air-gap can be improved by measuring the air gap with an air gap gauge accommodated in probe 8, using the results thus obtained for air-gap correction. This can be accomplished e.g. by arranging the coil on the iron core 11 of probe 8 in a way similar to the coil arrangement 1 to 5 on the measuring head. On iron core 11 an energizing coil 12 is accommodated, and by energizing the latter, voltage is induced in each of the sensing coils 14, 15 arranged on the two outside limbs of core 11 and connected in series and in sensing coil 13 located on the middle limb of iron core 11, directly beside the energizing coil 12. Subtracting the sum of voltages induced in the sensing coils from the voltage induced in sensing coil 13, a voltage proportional with the air gap between iron core 11 and measured surface is obtained.

Selection of the direction of excitation has an influence on the measuring accuracy.

Direction of excitation lies in the direction of the straight line connecting the limbs of yoke 6.

Direction of excitation lies in termed the direction of measuring the magnetic Barkhausen noise.

As is known, the direction and magnitude of the planar principal stresses can be determined from the magnetic Barkhausen noise measured in two directions perpendicular to each other.

It is expedient to perform the measurement in the direction of assumable principal stresses. In the bars of a lattice truss and in rails the direction of principal stresses of the residual manufacturing stresses and that resulting from loading occurring in service agree characteristically with the longitudinal direction of the beam or rail. From that follows that it is expedient to select one direction of the magnetic Barkhausen noise measurement to coincide with the length of the beam or rail, and its other direction to be perpendicular to the former.

When selecting the level of excitation an optimum has to be aimed at. In a test piece the level of excitation is considered optimum, by the application of which the change in magnitude of the signal will be maximum under the effect of a unit change of the tensile/compressive stress. The magnitude of this excitation level depends on the material under test, on its chemical composition, on its strength, etc. The typical value of this excitation level is 0.1 to 1 kA/m. Its determination may be performed—depending on the shape, homogeneity, and residual stress distribution of the test piece—by plotting a curve showing the correlation (function) between magnetic Barkhausen noise and level of magnetization, while gradually increasing the level of magnetization. The excitation level pertaining to the point of inflection of this function or to the average of points of inflection of the functions plotted in several points of the test piece will be the optimum excitation level pertaining to the given material.

The measuring results may be influenced by the residual manufacturing stresses, therefore it is expedient to reduce or eliminate their effect. One problem of determining the forces arising in the rods of lattice trusses or in rails is to eliminate the effect of manufacturing stresses affecting the measurements. It is a known regularity that in a cross-sectional area the forces and moments resulting from manufacturing stresses are balanced and their resultant is zero.

In the case of beams and rails the stresses appearing on their surface or near the surface reflect truly the stress distribution in the given cross-section.

The equilibrium mentioned above would provide possibility of determining the external force acting on a beam, if the measurements are performed over the cross-sectional area with sufficient density. In this respect experiments have been carried out on pieces taken from a 40×40×3 mm angle-steel beam of composition C15 specified by a respective Hungarian Standard (MSZ).

Figure 5:
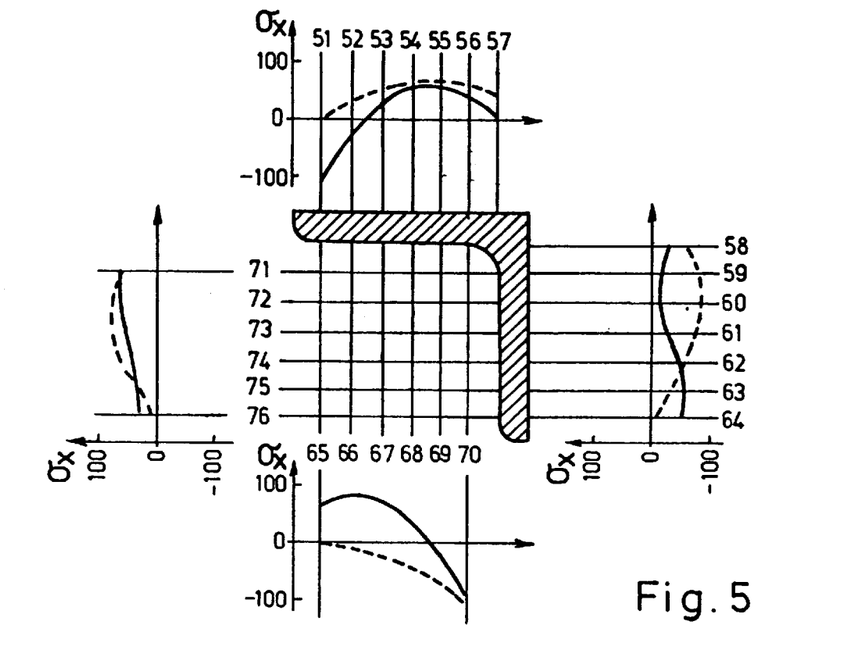
FIG. 5 shows longitudinal stress distribution in an angle steel, based on measurements performed in measuring points taken along the outline of two different cross-sectional areas.

In an angle-steel test specimen considerable residual stress may be present as a result of uneven quenching and of rolling. This is shown by the stress values obtained from the results of magnetic Barkhausen-noise measurements performed along a few cross-sectional areas after calibration mentioned above on the test specimen in a state free of any external force (FIG. 5). The range of values of these stresses is characteristically ±130 MHz.

Figure 6:
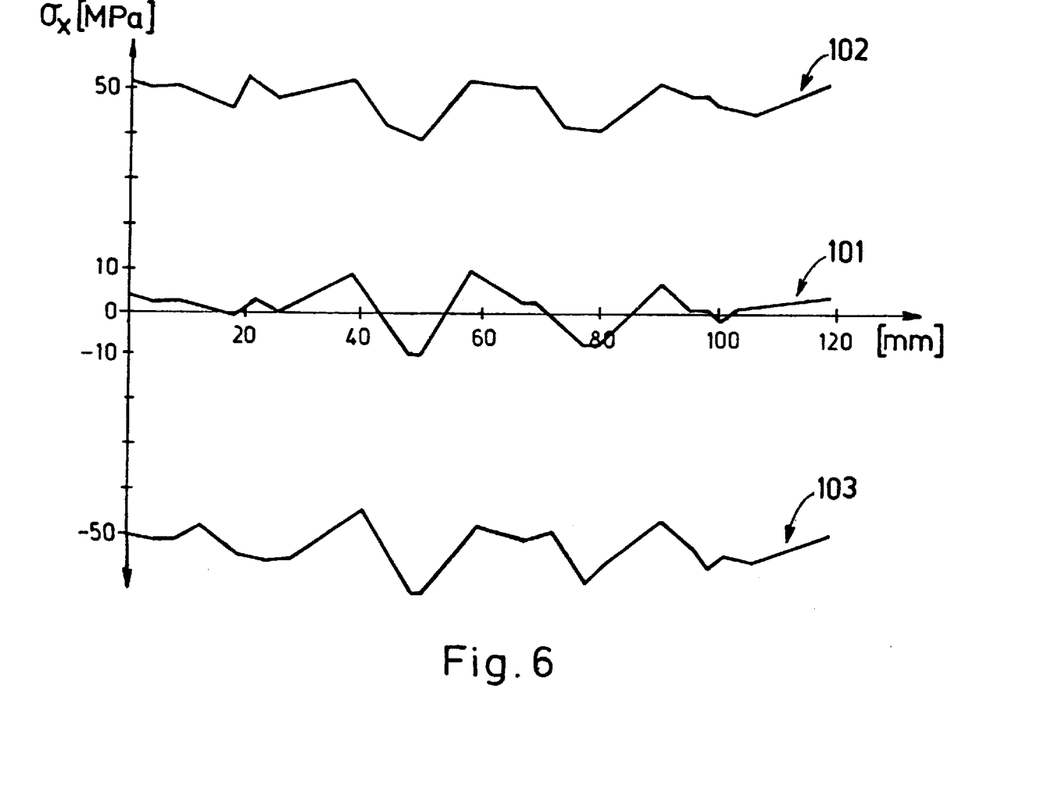
FIG. 6 shows variation of algebraic averages of longitudinal stresses arising in cross-sections taken along the length of an angle-steel test piece, as computed by way of calibration from the levels of longitudinal magnetic Barkhausen noise measured in the points shown in FIG. 5 of said test piece and plotted, free of external forces, in the stress states developing under compressive and pulling loading.
Figure 7:
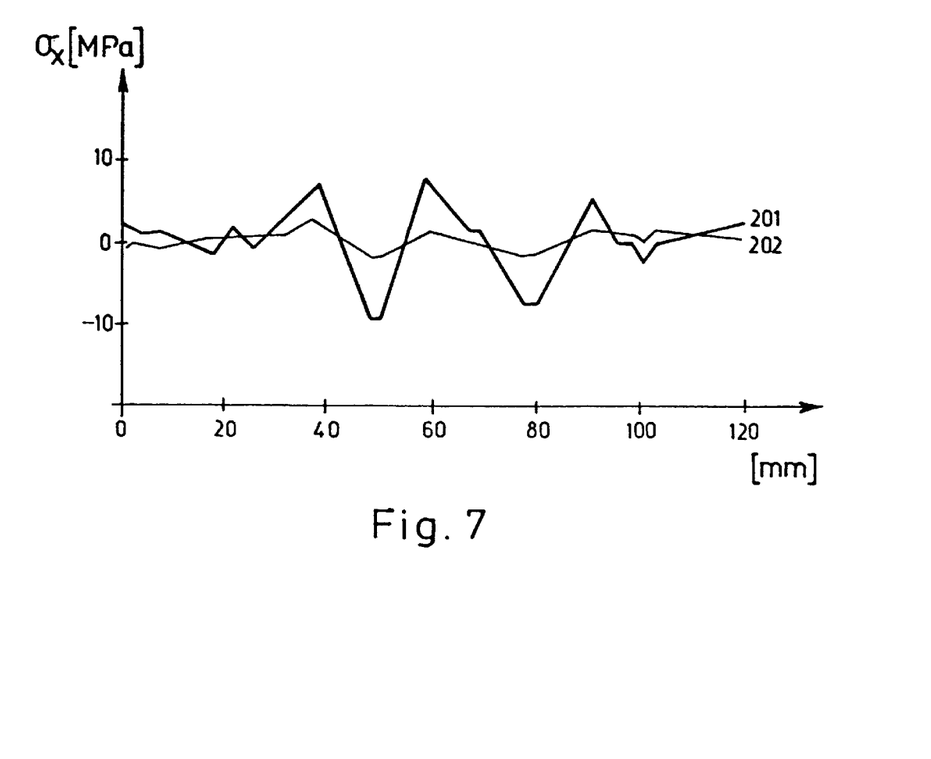
FIG. 7 is a diagram comparing the algebraic average (as shown in FIG. 6) of the longitudinal stresses pertaining to the unloaded state with the average of stresses obtained by weighting.

When the arithmetic mean of the results of measurements performed for several cross-sectional areas is formed, its change along the length of a specimen—according to our experience—is by one order of magnitude smaller (±10 MPa) than the changes taking place in the magnitudes of longitudinal stresses measured along the outline of the various cross-sectional areas (±130 Mpa) (line 101 of FIG. 6) or the changes of the stress along the length of the specimen measured at a single point of each cross-sectional area.

This average fluctuates around 0 MPa along the length of the test specimen, this being the consequence of proportionality existing between the longitudinal stresses measured along the outline and longitudinal stresses taken within the entire cross sectional area (termed volumetric longitudinal stresses).

When applying an external force to the test specimen, the arithmetic mean of the results obtained for each cross-sectional area shifts according to the stresses due to the applied external force. So, the changes taking place in the stress conditions due to an external force can be determined from the measurements performed along the outline and from the arithmetic mean of the measuring results obtained for each cross-sectional area (lines 102 and 103 of FIG. 6).

In the case when the superficial stress distribution fails to be proportional to the volumetric stress distribution, or when the superficial stress distribution is not measured in sufficient number along the outline, then weighting factors belonging to the various points can be determined experimentally and, forming weighted peripheral mean values by using these factors, these mean values can be made, on the one hand, proportional to the stress caused by the external force and, on the other hand, their fluctuation along the length of the test specimen can be minimized.

With the angle-steel test specimen mentioned, the lengthwise variation of averages determined for each cross-sectional area was reduced further, when—instead of the arithmetic mean of measuring results obtained for each cross-sectional area—weighting factors belonging to the numbered measuring points listed in the table shown below are used for forming the average values.

TABLE

| Serial number of measuring points | | Weighting factor | Serial number of measuring points | | Weighting factor |
| --- | --- | --- | --- | --- | --- |
| 51 | 64 | 0.8 | 65 | 76 | 0.8 |
| 52 | 63 | 0.9 | 66 | 75 | 0.85 |
| 53 | 62 | 1.15 | 67 | 74 | 0.9 |
| 54 | 61 | 1.2 | 68 | 73 | 0.95 |
| 55 | 60 | 1.2 | 69 | 72 | 1 |
| 56 | 59 | 1 | 70 | 71 | 1.05 |
| 57 | 58 | 0.9 | | | |

The accuracy of calculating the magnitude of stress generated by an external force and determined from the averages of measuring results obtained for each individual cross-sectional area can be improved further, if the averages of more cross-sectional areas are considered.

One of the difficulties of performing measurements is caused by the dependence of Barkhausen noise vs. stress relation upon the microstructure of the material. In the case of old bridges no samples can be taken from the rods of individual lattice trusses for the purpose of performing laboratory calibration, so a method called "local calibration" has been developed.

If the distribution of residual stress along the outlines of the cross-sectional area of a rod of a lattice truss is highly varying, then measurements are made at points, spaced apart as required, along the outlines of one or several cross-sections of the rod.

In the rod a change of stress of known magnitude is produced—e.g. by applying a test load and measuring the stresses by means of a strain gauge, the measurements are repeated at the same points as before. With rods of considerable residual stress the measuring accuracy can be improved by using a positioning template to ensure proper setting of the measuring head. After that, the magnetic Barkhausen noise is changed and detected in each measuring point to find the maximum of these changes in function of the level of Barkhausen noise.

Based on the change of noise and on the known stress variation the magnetic Barkhausen noise vs. mechanical stress curve is plotted, in the course of which the knowledge is made use of that at maximum change of magnetic Barkhausen noise the stress is zero.

In the rarely occurring case when the distribution of residual stress in the beam is considerably smaller than the range of stress variation to be investigated, it is sufficient to perform the measurement in one point but in several stress states of the beam.

Figure 8:
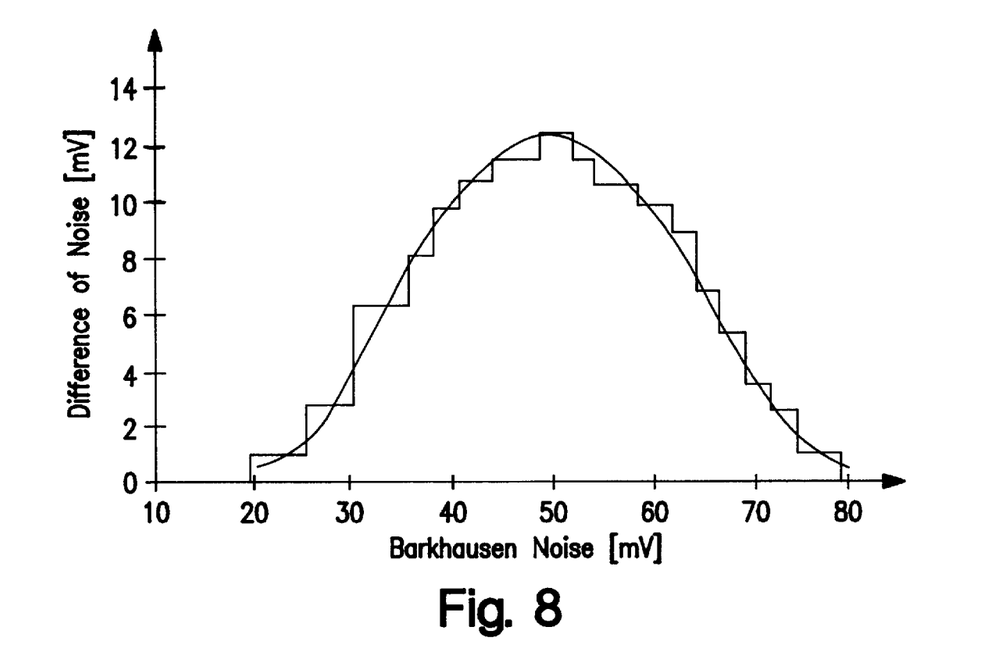
FIG. 8 shows variation of magnetic Barkhausen noise in the function of Barkhausen noise under the effect of a stress increase of 30 MPa measured on the angle-steel specimen in longitudinal direction.
Figure 9:
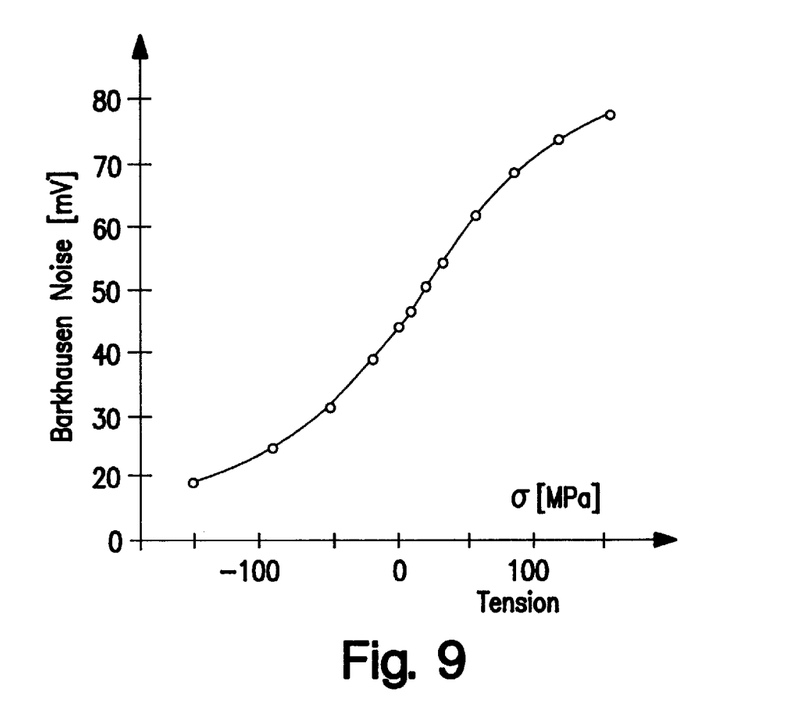
FIG. 9 illustrates the relation of magnetic Barkhausen noise determined from the histogram of FIG. 8 vs mechanical stress.

FIG. 8 shows for the above angle-steel sample the Barkhausen-noise differences plotted at known stress difference in function of the magnitude of noise. The calibration curve obtained by integrating the differences and reflecting the dependence of the Barkhausen noise upon longitudinal stress is shown in FIG. 9.

In a continuously welded railway track the displacement of rails is prevented by sleepers through track fastenings. After clamping of rails a known change of temperature will give rise to a thermal stress in the rails due to restricted dilatation. So, by performing measurements at one or more temperatures, the calibration curve can be plotted.

As resultant of the residual stress due to manufacturing technology and thermal stress caused by the restriction of dilatation, the direction of principal stress I arising in the rail lies in its longitudinal axis. Along the outlines of the rail the stresses perpendicular to the longitudinal axis are generally considerably lower than principal stress I. Therefore, at the periphery of the rail it is expedient to perform the magnetic Barkhausen noise measurements in longitudinal direction.

For testing a rail, the periphery of rail to be measured is made accessible, and depending on the number of measuring points the ballast is removed from under the rail as required by the size of the measuring head. The measuring-head positioning template matching to the rail of given type is fitted, and the position of template on the rail is marked in a permanent way when two or more temperatures are to be measured. The temperature sensor is fitted to the shaded side of the rail web near the measuring contour.

In the course of performing the variant of the measuring method complying with the invention and developed for the purpose of determining the neutral temperature of rails the following procedure has to be followed:

at the first temperature the longitudinal magnetic Barkhausen noise is measured along the periphery of the perpendicular cross-section of the rail, energized in longitudinal direction at least in two points of the railhead, at least in one point in the central part of the rail web, in the middle of the rail base, at the transition between head and web, and at the transition of rail base and web, the measurements are performed also in another stress state modified by a known amount (e.g. at the second temperature differing from the first, when from the temperature difference, with the coefficient of thermal expansion, the modulus of elasticity and cross-sectional area being known, the change of the resultant of longitudinal stresses, i.e. change of loading, can be determined), the change of magnetic Barkhausen noise is then determined for each measuring point and the maximum of changes in the function of magnetic Barkhausen noise level is established, based on the variation of noise and on the known stress difference, the stress vs. magnetic Barkhausen noise calibration curve is plotted, utilizing the known fact that the point where the change of magnetic Barkhausen noise is maximum corresponds to the zero-stress state, from the magnetic Barkhausen noise obtained for each measured point, in one of the two stress states the stresses belonging to each point are determined by means of the calibration curve, from the weighted average of stresses the resultant stress in the investigated cross-section of rail is determined (the weighting factors shall be established in the course of tests previously performed on rails of identical manufacture and shape), from the resultant stress, first temperature, coefficient of thermal expansion and modulus of elasticity, the neutral temperature of the rail is determined.

The stress state can be modified also by imposing an additional force on the rail by applying a pulling or compressive force to produce a change in the stress state. The change of stress state can be determined by measuring the force exerted by the element used for applying the force, and from the known cross-sectional area, or by means of some tensiometer means located in the measuring points and from the known modulus of elasticity of the investigated test piece.

At each point the value of longitudinal stress defined from the magnetic Barkhausen noise can be corrected by the magnitude of transverse stress that can be established from the excitation acting crosswise with respect to the longitudinal direction and from the magnetic Barkhausen noise generated thereby.

The weighting factors used in the weighted summation of stresses belonging to the various measuring points and obtained from the measuring results by computation may be determined empirically. For that determination the rail of given geometry can be brought into different stress states e.g. by means of a drawbench, and the weighting factors can be determined in a few steps.

By increasing of the number of measuring points the determination becomes more accurate, but it is not worth while to measure at more than 30 measuring points. According to our experience, satisfactory degree of accuracy can be obtained by 14 measuring points (3 on the railhead, 2 at the junction of railhead and web, 2 on the rail web, 2 at the junction of web and foot, 1 in the middle of the foot, 2 at either edge of the foot).

The measurement can be arranged so that several measuring heads are attached suitably positioned corresponding to the required measuring points, whereby the measuring time may considerably be reduced. The measuring system can be mounted on a carriage or vehicle movable over the rail. The position of measured cross-sections can be assigned by means of a route signal transmitter 501. The measurement can be performed intermittently or in such a way that, while the carriage is kept in continuous forward motion, the measuring head system is brought to a halt with respect to the rails, and for the time of measurement the head system slides backwards with respect to the carriage moving backward over a guide rail mounted on the carriage, then after the measuring system having been pushed forward, a new measurement can be performed.

Figure 10:
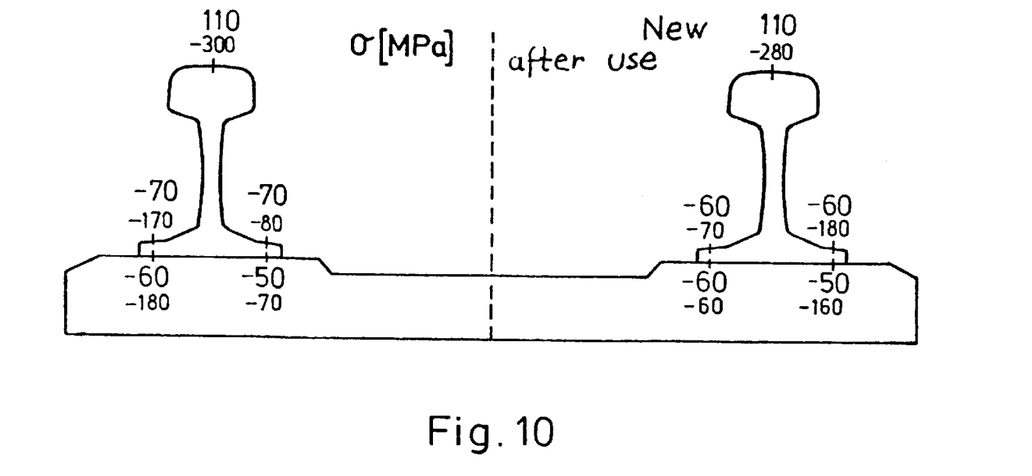
FIG. 10 shows rearrangement of residual manufacturing stresses on railheads and at the top and bottom sides of rail flanges of welded tracks.

The optimum number of measuring points and the weighting factor pertaining to each measuring point have been determined in the above way for the 54 kg/m type rails manufactured by Diósgyör (Hungary) and installed for MAV (Hungarian State Railways). These weighting factors have been used e.g. for determining the effect of changes in the values of residual stresses under the influence of railway traffic that have taken place in a new track of a railway line (FIG. 10).

Figure 11A:
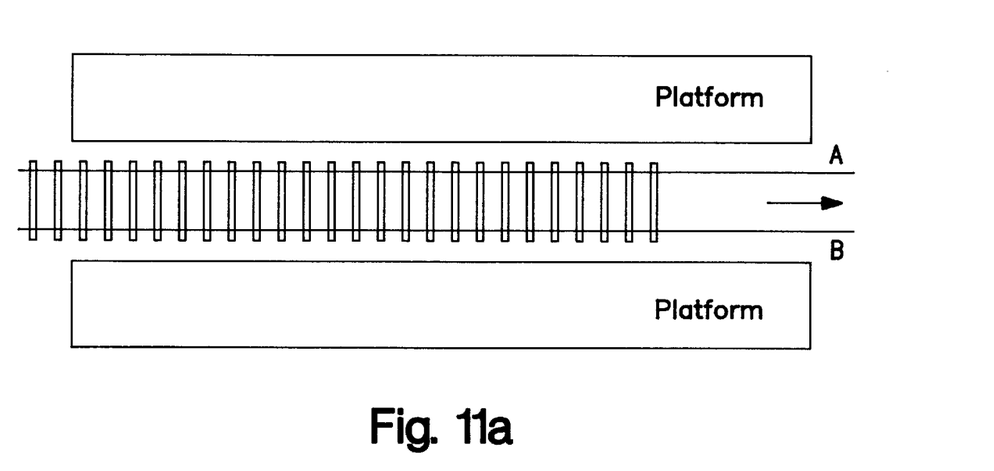
FIG. 11a and 11b is the top view of a braking section of a railway track, showing longitudinal distribution of neutral temperature of rails and changes taking place in the distribution of the same after ballast screening, as well as the relation between said distribution and the location of rail buckling.
Figure 11B:
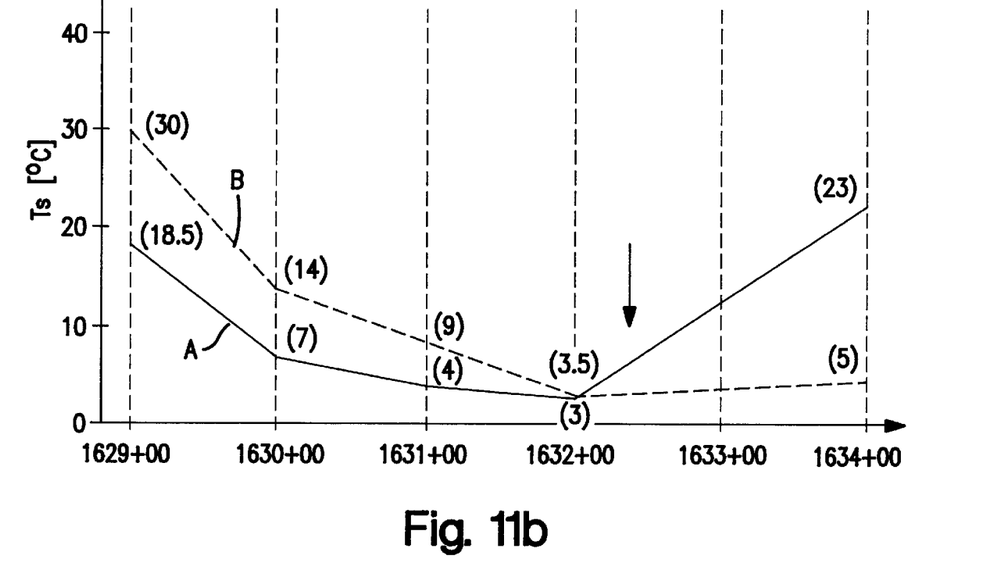

An example of determining the neutral temperature in the running line of a railway station is shown in FIG. 11. Beside the top view of platforms shown in FIG. 11a, the track section laid in concrete trough is illustrated, and the longitudinal distribution of neutral temperature of the welded rail determined by the described method is to be seen in FIG. 11b. Within the section shown a very low neutral temperature minimum can be observed, which is the consequence of material congestion due to regular braking over this section. In the course of a maintenance operation performed soon after the above investigation the ballast was screened without substantial influence on the distribution of neutral temperature. At the same time, due to ballast screening, the lateral resistance of ballast decreased, so that in the vicinity of neutral temperature, the rail could move in lateral direction, avoiding thereby the compressive stresses caused by the longitudinal thrust arising under the effect of high temperatures.

We claim:

1. A method for determining in situ a longitudinal load acting on a beam exposed to a longitudinal load, wherein the beam is energized longitudinally in an acoustic frequency range, and a level of magnetic Barkhausen noise is measured at a surface of the energized region, then a calibration curve of Barkhausen noise versus longitudinal loading is established by measuring Barkhausen noise at different longitudinal stress states, the method comprising the steps of:

establishing the calibration curve by measuring in situ the level of the magnetic Barkhausen noise at least at two different loadings and at least at three points on a periphery of a cross section of the beam;

plotting a function of a value of the Barkhausen noise versus the change in Barkhausen noise for the change of the local stresses of said at least two different loadings, furtheron assigning the value of the Barkhausen noise belonging to zero stress to the value at the location of maximal change of the function, establishing the curve of Barkhausen noise versus stress by integrating the function of change of the Barkhausen noise versus Barkhausen noise, defining the stress at the given point of the cross section of the beam, then repeating the previous steps at further similarly loaded cross sections and for each point defining a weighting factor providing a weighted average of stresses in the same cross section corresponding to the given loading, and defining the longitudinal loading falling onto said given cross section on the basis of said calibration curve and by carrying out a weighted average calculation.

2. The method as claimed in claim 1, wherein the beam is a railway rail, and further comprising the steps of determining a neutral temperature of the railway rail by considering the modulus of elasticity, coefficient of thermal expansion and temperature of the rail.

3. The method as claimed in claim 1, wherein the energization is directed perpendicular to the measured cross-section through two spaced apart regions and the magnetic Barkhausen noise leaving the surface is measured between these two regions at the investigated cross-section.

4. The method as claimed in claim 3, further comprising the steps of producing said energization by a flux generated by means of a magnetic yoke fitted to the surface, and by regulating the magnitude of flux emerging from the ends of the yoke fitted to the investigated surface.

5. The method as claimed in claim 4, wherein the steps of measuring the magnetic Barkhausen noise at the investigated surface is carried out with a sensor fitted to the cross-section and containing a ferromagnetic material, and an air gap between said ferromagnetic material and the investigated surface is measured, and correcting the magnitude of the detected magnetic Barkhausen noise according to the measured depth of the air gap.

6. Equipment for determining a longitudinal load of beam exposed to a longitudinal load, comprising:

an audio-frequency energizing unit (301);

a magnetic sensor (404) that is arranged and constructed to be magnetically coupled to the beam to be tested;

a frequency-selective measuring (302) unit connected to said magnetic sensor (404) and sensitive to frequencies higher than those generated by said energizing unit;

a computer (306) for computing results from the measured values;

an air gap gauge (403) for detecting an air gap depth of spacing between said magnetic sensor and a surface of the beam to be tested, said air gap gauge (403) being connected to said computer (406) for correcting a measured value of Barkhausen noise in dependence on the air gap depth;

the energizing unit (301) comprising an energizing coil (1) on a magnetic yoke (6), and a sensing coil system with plural sensing coils (2, 3 and 4, 5 respectively) on the magnetic yoke (6) beside the energizing coil (1) at the surfaces of the magnetic yoke (6) and that are arranged and constructed to be brought into contact with the beam to be tested, said magnetic sensor (404) comprising a coil system arranged on an at least three-limb ferromagnetic iron core (11) and containing at least two coils (9, 10), all these being accommodated in a measuring head (400), said air gap gauge comprising an energizing unit arranged on the three-limb iron core (11) of the magnetic sensor (8) and a detector for sensing the stray flux generated by the energizing unit.

7. Equipment claimed in claim 17, wherein the energizing unit comprises an energizing coil (12) arranged on the three-limb iron core (11) of the magnetic sensor, and a detector sensing the stray flux induced by the energizing unit and comprising sensing coils (13, 14, 15) accommodated on the three-limb iron core (11) of the magnetic sensor.

* * * * *